United States Patent [19]

D'Silva

[11] Patent Number: 5,543,618
[45] Date of Patent: Aug. 6, 1996

[54] CAPILLARY ZONE ELECTROPHORESIS-MASS SPECTROMETER INTERFACE

[75] Inventor: Arthur D'Silva, Ames, Iowa

[73] Assignee: Iowa State University Research Foundation, Inc., Ames, Iowa

[21] Appl. No.: 268,501

[22] Filed: Jun. 30, 1994

[51] Int. Cl.⁶ .............................. B01D 59/44; H01J 49/00
[52] U.S. Cl. .............................................. 250/288; 250/282
[58] Field of Search ................................ 250/288, 288 A, 250/281, 282

[56] References Cited

U.S. PATENT DOCUMENTS

| | | | |
|---|---|---|---|
| 4,675,300 | 6/1987 | Zare et al. | |
| 4,842,701 | 6/1989 | Smith et al. | 250/281 |
| 4,885,076 | 12/1989 | Smith et al. | 250/288 |
| 4,994,165 | 2/1991 | Lee | 204/299 R |
| 5,006,210 | 4/1991 | Yeung et al. | |
| 5,162,651 | 11/1992 | Kato | 250/281 |

OTHER PUBLICATIONS

E. J. Guthrie et al., *Anal. Chem.*, 56, 483–486 (1984).
P. Jandik et al., *LC GC, The Magazine of Separation Science*, 9, 634–645 (1991).
J. W. Jorgenson et al., *Anal. Chem.*, 53, 1298–1302 (1981).
J. W. Jorgenson et al., *Science*, 222, 266–272 (1983).
E. D. Lee et al., *J. Chromatogr.*, 458, 313–321 (1988).
E. D. Lee et al., *Biomed. Environ. Mass Spectrom.*, 18, 844–850 (1989).
F. E. P. Mikkers, *J. Chromatogr.*, 169, 11–20 (1979).
M. A. Moseley et al., *J. Chromatogr.*, 516, 167–173 (1990).
J. D. Olechno et al., *American Laboratory*, 23, 58–62 (1991).
J. A. Olivares et al., *Anal. Chem.*, 59, 1230–1232 (1987).
V. Pretorius et al., *J. Chromatogr.*, 99, 23–30 (1974).
R. D. Smith et al., *Anal. Chem.*, 60, 436–441 (1988).
R. D. Smith et al., *Anal. Chem.*, 60, 1948–1952 (1988).
T. Tsuda et al., *J. chromatogr.*, 248, 241–247 (1982).
T. Tsuda et al., *J. Chromatogr.*, 264, 385–392 (1983).

*Primary Examiner*—Bruce C. Anderson
*Attorney, Agent, or Firm*—Schwegman, Lundberg, Woessner & Kluth, P.A.

[57] ABSTRACT

A device for providing equal electrical potential between two loci unconnected by solid or liquid electrical conducts is provided. The device comprises a first electrical conducting terminal, a second electrical conducting terminal connected to the first terminal by a rigid dielectric structure, and an electrically conducting gas contacting the first and second terminals. This device is particularly suitable for application in the electrospray ionization interface between a capillary zone electrophoresis apparatus and a mass spectrometer.

20 Claims, 1 Drawing Sheet

CAPILLARY ZONE ELECTROPHORESIS-MASS SPECTROMETER INTERFACE

STATEMENT OF GOVERNMENT RIGHTS

This invention was made with the support of the U.S. Government under United States Department of Energy Contract No. W-7405-Eng82. The Government has certain rights in the invention.

FIELD OF THE INVENTION

This invention relates to a device for providing equal electrical potential, in particular grounding, between two loci unconnected by solid or liquid electrical conductors. In particular, the electrical continuity between the two loci is provided by an electrically conducting gas. This invention is particularly applicable in the interface of capillary zone electrophoresis apparatus and a mass spectrometer.

BACKGROUND OF THE INVENTION

Electrophoresis is an electrochemical process in which molecules with a net charge migrate in a solution under the influence of an electric current. It is a powerful technique for the separation and analysis of charged substances. A very important factor in the widespread use of electrophoresis is the utilization of stabilizing media such as polymer gels. This stabilizing media stabilizes the separation media (i.e., the liquid media through which the charged molecules migrate e.g., a buffer) against convection and flow which would otherwise disrupt separations. The microporous nature of stabilizers permits the electromigration of molecules through the stabilizers. However, because of the presence of particulates of various size and channels, stabilizers can cause zone broadening because of eddy migration and extensive adsorption between solutes and the stabilizer, for example. There is a desire to eliminate the use of such gels and adapt electrophoresis to on-line sample analysis, detection, quantification, and automated operations.

One automated version of electrophoresis that has been developed uses an open capillary tube, i.e., a tube typically made of fused silica containing a buffer without a stabilizing medium. In such a system, electrophoresis can take place with minimal interference and zone broadening can be minimized. The capillary acts like the microporous gel to counteract convective flow. Thus, the stabilizing effect of the capillary increases as the capillary diameter is decreased. This decrease in diameter of the capillary increases the surface to volume ratio and thus enhances heat dissipation.

In capillary electrophoresis, a buffer filled capillary is suspended between two reservoirs filled with buffer. Typical capillary diameters are less than 80 microns and typical lengths are more than one meter. An electric field is applied across the two ends of the capillary. Samples are introduced at the high potential end, which, under the influence of the electrical field, migrate toward the low potential end. When the samples leave the capillary zones after migrating through the capillary, they are detected by a detector.

In capillary zone electrophoresis (CZE), a sample zone is eluted by a carrier electrolyte. The carrier constituents have the same charge as the sample constituents to be separated. Separations are based upon differences in the electrophoretic mobilities of the constituents. Thus, significantly high resolution separations can be obtained and manipulated by changing the electrophoretic medium (e.g., pH and buffer composition).

Capillary zone electrophoresis provides a system for exploring the use of nonaqueous separation media. Furthermore, the elimination of a user gel or particulate system in the capillary enables the separation of large biomolecules and particulate-containing samples, such as viruses, cells, and organelles. CZE is limited, however, because of the limited availability of on-line detection methods. For further development and application of capillary zone electrophoresis, on-line electronic detection systems permitting good quantification are needed. Furthermore, there is a need for extremely sensitive detectors and particularly detectors of higher sensitivity than can be used on samples containing particulates.

Typically, ultraviolet-visible (UV-vis), fluorescent, or conductivity detection methods are used for detection of the species eluted in CZE. These detection methods have severe volume and sample size limitations, however, which present a major drawback in the use of CZE for the separation of complex mixtures. The ideal detectors for CZE should provide universal detection, selectivity, and sensitivity without degrading separation efficiency. Thus, mass spectrometry seems to be highly compatible with CZE.

In the on-line combination of CZE and mass spectrometry, the interface is typically accomplished by the application of electrospray ionization techniques. See, for example, J. A. Olivares et al., *Anal. Chem.*, 59, 1230–1232 (1987). A strong electroosmotic flow in CZE (e.g., generally about 1 µl/min), which results from a large potential applied across the capillary, is highly compatible with conventional mass spectrometers. The potential drop across the CZE column is typically ±30 kilovolts per meter. This potential drop is sufficiently large to result in the elution of ions, and to provide an electrospray. E. D. Lee et al., *J. Chromatography*, 458, 313 (1988) and *Biomed. Environ. Mass. Spectrum.*, 18, 253 (1989) also disclose the successful coupling of CZE with mass spectrometry utilizing atmospheric pressure ionspray interface, which is similar to electrospray ionization.

Although mass spectrometry is well-suited by analyzing eluates of capillary zone electrophoresis (CZE), a key element of the CZE-MS interface is the provision for electrical contact of the buffer at the capillary exit. Typically, a thick silver layer is deposited at the end of the capillary. Furthermore, in the application of CZE, the high voltage end is immersed in the sample and the opposite end is grounded as a part of the detection system. With a mass spectrometer, however, the detector end has to be inside a high vacuum chamber, and therefore cannot be easily grounded. Thus, there exists a need for a detection system in which good grounding is provided to the exit end of the capillary in a vacuum condition when CZE is interfaced with a mass spectrometer.

SUMMARY OF THE INVENTION

The present invention relates to a device for providing equal electrical potential between two loci unconnected by solid or liquid electrical conductors. The device comprises a first electrical conducting terminal, a second electrical conducting terminal and an electrically conducting gas contacting both the first and the second electrically conducting terminals. The two terminals are held in a fixed position in relation to each other by a dielectric rigid structure. The electrical continuity between the first and second terminals is provided by the electrically conducting gas. Typically, the electrically conducting gas is an ionized inert gas, preferably argon, although other gases may be ionized to provide the same function. The ionization of the gas is typically by means of alpha particles emitted by thorium from $ThO_2$ in monazite sand.

Also provided is a electrospray ionization interface (ESI) suitable for use in the CZE-MS interface and a method of making such an interface. This invention is particularly suitable for application to provide a grounding for the ESI between the capillary zone electrophoresis (CZE) capillary and the vacuum chamber of the mass spectrometer (MS). Mass spectrometers are well-suited for application in the analysis of analytes in CZE. However, because mass spectrometer functions in a vacuum, it is necessary that the exit end of the ESI be under vacuum. The present invention provides a device for grounding the ESI such that the ESI or its electrical connection will not be easily damaged by vibrations, etc.

In a preferred embodiment of the present invention, a layer of silver paint is painted on the exit end of the CZE capillary to form the first electrical conducting terminal. The paint extends into the lumen of the capillary so that it provides an electrical continuity between the eluant in the capillary and the first terminal. A glass tube is affixed on the exit end of the capillary, surrounding it. The shoulder of the glass tube distal to the exit end of the capillary is sealed around the capillary except for an inlet fitting through which a gas enters the glass tube. The gas is preferably an inert gas, and more preferably argon. The end of the glass tube is fitted or deposited with a metal layer, which is connected to electrical ground. A sidearm in the glass tube contains thorium oxide, which emits alpha particles. Obviously, other sources of alpha particles or beta particles (such as a metal, e.g., thorium or nickel, foil) can also be used. The alpha (or beta) particles ionize the gas, providing electrical continuity between the first and second terminals.

DETAILED DESCRIPTION OF THE INVENTION

Figure 1:
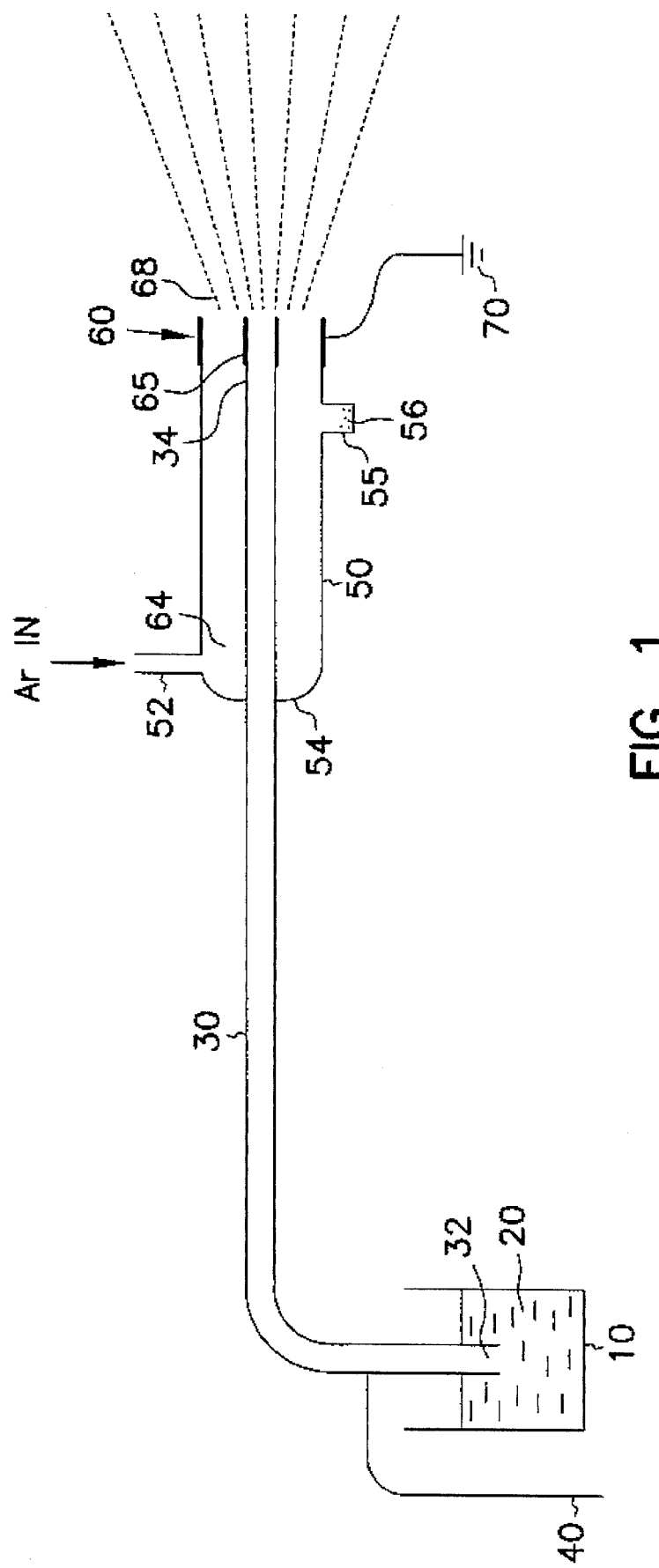
FIG. 1 shows the structure of an electrospray ionization interface of the present invention.

The present invention provides a device for providing equal electrical potential between two loci unconnected by solid or liquid electrical conductors. More particularly, the present invention provides a device for grounding the exit end of a capillary in capillary zone electrophoresis, interfaced with a mass spectrometer, utilizing an ionized gas as a conductor. The present invention also provides a method for providing equal electrical potential between two loci using an ionized gas as a conductor, particularly in the grounding of the exit end of the capillary in capillary zone electrophoresis in a CZE-MS interface. Detailed embodiments of the invention are disclosed herein. However, it is to be understood that the disclosed embodiments are merely exemplary of the present invention, which may be used in various systems. Specific details disclosed herein are not to be interpreted as limiting, but rather as a basis for the claims and as a representative basis for teaching one skilled in the art.

In CZE, a high voltage is applied across a capillary, which is typically made of fused silica and coated with polyamide, although other nonconducting materials such as organic polymers, e.g., a thermoplastic polymer, can be used. The scope of this invention is not bound by the particular choice of the material of the capillary.

As mentioned earlier, the efficiency of separation of molecules improves as the diameter of the capillary increases. Other factors as well affect the improvements in electrophoretic capillary ion analysis. One factor is the electroosmotic flow condition, which is affected by the concentration of constituents of the carrier buffer. Different buffers can be used for the separation of different solutes. For example, a nominal pH 9 phosphate buffer of 0.01M concentration can be used for separation of amino acids from a mixture containing lysine, methionine and glycine. Of course, the concentration of the constituents of the carrier and the pH can be varied to suit the need for the separation of the particular sample. For example, in other instances, acetate buffer, a buffer concentration at 0.05M, or a pH 9.5 buffer may be used. Modifiers such as acetonitrile or methanol may also be used to increase the sensitivity in CZE because methanol and acetonitrile, having lower dielectric constants than water, tend to facilitate ion emission from small droplets. It is believed that high concentrations of buffer salts prevent the reduction of droplets to a small enough size for analysis by certain detection methods. Again, the application of this invention is not bound by the choice of buffers and the particular scientific theory thereof.

Typically, CZE is conducted by use of a capillary with automated electroosmotic sample introduction at the high voltage end, although it is possible to practice CZE by applying a high voltage in such a way that the low voltage end is the end where the sample is introduced into the capillary. Preferably, the potential between the two termini of the capillary is about 10–60 kV, more preferably, about 25–35 kV. Typically, capillary zone electrophoresis is carried out with a 0–60 kV DC power supply. This high voltage power supply is typically maintained between −38 and +38 kilovolts, while the MS probe tip is maintained at a potential of 8 kilovolts for detection of positive ions and −8 kilovolts for the detection of negative ions. Examples of useful power supplies for applying such a voltage are a Model LG60P2.5 DC power by Glassman High Voltage, Inc. and Model RHR60P30/EI DC power supply by Spellman.

Of the various methods that are available for analyzing the effluent from CZE, all have their limitations. Mass spectrometry, however, appears to be ideally suitable for such analyses. Mass spectrometry separates gaseous ions of differing mass and charge by the action of electric and magnetic fields. The separation is based on the mass to charge ratio. This technique can be used to measure the relative abundance of various ions in a mixture. The mass spectrometer comprises a source where ions are generated, a means for separating the ions according to mass/charge ratio, and a means for collecting the ion beams. The separation of the ions takes place in an analyzer tube under a magnetic field. Gaseous particles in the analyzer tube tend to hinder the movement of the ions as they travel through the tube. In order to achieve maximal sensitivity and stability, it is therefore necessary for the mass spectrometer to operate under vacuum condition. For example, in a typical mass spectrometer, such as SCIEX TAGA 6000E triple-quadruple mass spectrometer (Thornhill, Ontario, Canada), high vacuum is achieved by cryogenically cooled surfaces maintained at 15–20K surrounding the quadruple mass filter. Operation is often at $10^{-5}$ torr to $10^{-6}$ torr.

A reliable interface between capillary zone electrophoresis and a mass spectrometer will lead to a more readily automated system utilizing capillary zone electrophoresis for analysis. With the recent development of spray ionization interface for interfacing capillary zone electrophoresis and mass spectrometry, the adaptation of CZE for automated analyses of complex molecules is becoming reality. In the application of capillary zone electrophoresis, typically, the high voltage end is immersed in the sample and the opposite end, where the samples exit the capillary, is grounded. In some cases, the exit end may be held to about ±3 kV for positive or negative ion operation when electrospray ionization is utilized to interface the CZE with MS.

In CZE, often the exit end of the capillary is grounded and forms part of the detection system. The above arrangement is adequate when an on-line detector such as a laser induced fluorescence detector is utilized. However, when a CZE capillary is to be interfaced to a mass spectrometer the detector end has to be inside a high vacuum chamber and a new grounding technique is needed. When a capillary zone electrophoresis capillary is interfaced in a mass spectrometer, the species in the eluant of the CZE need to be in ionized form before detection by the MS. For polar and ionic compounds, this can be achieved by mechanisms such as fast atom bombardment (FAB) and electrospray ionization. In electrospray ionization the eluants with the carrier buffer are drawn through the electrospray ionization interface (ESI) by an applied electrical potential to form a spray as they exit the ESI. The description of applicable electrospray techniques in J. A. Olivares, *Anal. Chem.*, 59, 1230 (1987), which is incorporated herein by reference. It is also possible, and sometime preferable to assist the nebulization of the effluent from the ESI into a fine aerosol by means of injection of an inert gas, for example, nitrogen, into the ESI. Typically, nitrogen is introduced into the ESI before the exit by means of a side port such that the effluent exits the end of the ESI electrode at a velocity of about 300 meters per second.

In the interface of CZE with MS, the detector end of the electrospray ionization interface has to be inside a high vacuum chamber and therefore cannot easily and sturdily be grounded or electrically connected to a terminus. If the capillary is interfaced directly with the mass spectrometer without a separate intermediate device, the exit end of the capillary has to be placed in a vacuum. This gives rise to a need for a good grounding device for the exit end of the capillary. In some cases, to provide ground or maintaining the exit terminus of the capillary or the electrospray ionization interface at a potential, a stainless steel tubing has been fitted to the exit terminus and a layer of metal, typically silver, deposited over the stainless steel tubing and the end of the capillary. The construction, however, is not mechanically sturdy because the stainless tubing is small and the junction between the silver deposit and the stainless steel is weak and easily damaged. The present invention relates to a system that provides good grounding to the exit end of the capillary in a vacuum condition when capillary zone electrophoresis is interfaced with a mass spectrometer.

This invention is particularly useful for providing electrical continuity between two terminals which are not connected to each other by means of solid or liquid electrical conductors. The device comprises a first terminal and a second terminal that are maintained at equal electrical potential. In the preferred embodiment of the electrospray ionization interface between CZE and MS, to achieve separation in the capillary zone electrophoresis and forming a spray at the exit end of the capillary, it is necessary to maintain the exit end of the capillary, the first terminal, at a stable potential, preferably at −30 kV to 30 kV, and more preferably at ground potential. To create a good electrical connection that is sturdy and not easily broken or weakened by mechanical force, it is preferable to have no solid connection between the first terminal and a second terminal that is connected by means of a solid electrical conductor to the pole of potential between −30 kV and 30 kV. Often, it is desirable to maintain this pole at ground potential.

To accomplish good, mechanically sturdy grounding of the capillary indirectly and still have the CZE functioning properly a new interface is used. Such an interface is shown in the FIG. 1.

Referring to FIG. 1, which shows the apparatus for the interfacing of CZE with MS, the intake end 32 of the capillary zone electrophoresis capillary 30 is immersed in a buffer solution 20 in a container 10. The eluant in the end is connected to a high voltage power supply 40, typically at the positive end. The grounding end 34, i.e., the exit end in the preferred embodiment, of the CZE capillary 30 is coated with a conducting silver paint. This forms what is referred to herein as the first electrical conducting terminal 65. The paint extends slightly into the inside of the capillary such that it contacts with the eluting compounds 68. The capillary is surrounded with a glass tube 50. The shoulder 54 of the glass tube joins in and seals around the capillary 30. An inlet fitting 52 is attached to the shoulder, permitting the inflow of the argon gas into the space 64 between the glass tube and the capillary. A metal tip 60 is epoxy-glued to the exit end of the tube. This is referred to herein as the second electrical conducting terminal. A small sidearm 55 in the tube contains monazite sand 56, which contains $ThO_2$. Argon gas at an appropriate flow rate, typically about 15 ml/min for a capillary tube of 1 m long, is introduced into the outer tube 50 through the inlet fitting 52. The alpha particles emitted from the thorium in the monazite sand 56 ionize the argon gas and generate a conducting path between the silver paint 65 and the metal tip 60 of the outer tube 50 and thus to ground 70.

With this arrangement the analyte 68 eluting from the capillary can also be nebulized into a fine aerosol which is emitted inside the vacuum chamber of the mass spectrometer. As mentioned above, the effluent from the ESI can also be nebulized by the assistance of nitrogen gas injection. With proper nebulization, a fine aerosol can be formed. When this fine aerosol is emitted into the mass spectrometer, the vacuum condition will readily desolvate the eluant. This will contribute to the increased sensitivity of the analysis. An eluant volume of the size of nanoliters is readily desolvated inside the vacuum chamber and can be analyzed with high sensitivity with the mass spectrometer.

Thus, the device of the present invention provides equal electrical potential between two loci unconnected by solid or liquid electrical conductors. Typically, the electrically conducting material on the end of the outer glass tube 50, i.e., the second terminal, is a layer of vapor-deposited silver. This material can also be an electrically conducting paint painted onto the tip extending into the lumen of the end of the tube. Also, typically, the first terminal is a layer of electrically conductive paint, preferably silver paint. Although electrically conducting silver paint and vapor deposited metal were given in the above-mentioned embodiments as illustrations, other metal deposit, electrically conducting paint, or ways to attach a electrically conducting material to the capillary end and the end of the outer tube can be used, for both the first and second terminals. For example, gold can be vapor-deposited in a similar manner as silver. A metal or alloy may also be fitted to the end of the capillary or glass tube. In the case where an electrospray ionization interface separated from the CZE capillary is used, where such ESI capillary is not directly a continuation of the CZE capillary, the present invention may be applied to the exit end of the capillary of the ESI in a similar manner as is done for the CZE capillary as aforementioned.

An electrically conducting gas is used to provide an equal potential between the first terminal 65 and the second terminal 60, which are connected by a rigid dielectric structure, i.e., glass tube 50. Preferably, an ionized inert gas, e.g., Ar, He, Ne, is used as the electrical conductor between the first and the second terminals, although other ionized gases such as ionized air, nitrogen, etc., may be used. The preferred inert gas is argon. The conductivity of the ionized gas depends on the flow rate and reactivity of the gas, the volume of the gas being ionized, and the amount and energy of the alpha particles.

In a preferred embodiment, alpha ($\alpha$) particles are used to ionized the argon. In a more preferred embodiment, $\alpha$ particles emitted from thorium are used to ionize argon, although other sources of $\alpha$ particles can be used. In a preferred embodiment, monazite sand, which contains $ThO_2$, is used as a source of thorium for emitting the alpha particles.

It will be understood that even though numerous characteristics and advantages of the invention have been set forth in the foregoing description, together with details of the structure and function of the invention, the disclosure is for illustration only. Changes may be made in detail within the broad principle without departing from the spirit and scope of the present invention. The complete disclosures of all patents, patent documents, and publications are incorporated herein by reference.

What is claimed is:

1. A device for providing equal electrical potential between two loci unconnected by solid or liquid electrical conductors comprising:
   (a) a capillary tube having an exit end;
   (b) a first electrical conducting terminal positioned on the exit end of the capillary tube;
   (c) a rigid dielectric structure surrounding the exit end of the capillary tube and the first electrical conducting terminal; and
   (d) a second electrical conducting terminal positioned on the rigid dielectric structure so as to provide electrical continuity between the first terminal and the second terminal in an electroosmotic circuit when an electrically conductive gas contacting both the first terminal and the second terminal is present in the rigid dielectric structure.

2. The device of claim 1 wherein the capillary tube has a lumen, and the first electrical conducting terminal contacts the lumen of the capillary tube.

3. The device of claim 1 wherein the first electrical conducting terminal comprises a layer of metal deposited on the exit end of the capillary tube.

4. The device of claim 1 wherein the first electrical conducting terminal comprises a layer of electrically conducting paint on the exit end of the capillary tube.

5. The device of claim 1 wherein the second electrical conducting terminal is connected by a solid electrical conductor to a pole of potential maintained between about −30 kV and 30 kV.

6. The device of claim 5 wherein the pole is maintained at about ground potential.

7. The device of claim 1 wherein the exit end of the capillary tube is interfaced with a mass spectrometer.

8. The device of claim 1 wherein the rigid dielectric structure comprises a glass tube.

9. The device of claim 8 wherein the second electrical conducting terminal comprises a metal layer deposited on the glass tube.

10. The device of claim 8 wherein the glass tube has a shoulder distal to the exit end of the capillary tube, which shoulder is sealed around the capillary tube.

11. A method for detecting the presence of a target species in an eluent during capillary zone electrophoresis comprising the steps of:
    (a) providing a capillary tube containing an eluent and having an exit end;
    (b) providing a first electrical conducting terminal contacting the exit end of the capillary tube and the eluent therein;
    (c) providing a rigid dielectric structure surrounding the exit end of the capillary tube and the first electrical conducting terminal;
    (d) providing a second electrical conducting terminal positioned on the rigid dielectric structure;
    (e) filling the rigid dielectric structure with an electrically conducting gas such that the gas contacts both the first terminal and the second terminal;
    (f) electroosmotically moving a target species through the capillary tube such that it exits the capillary tube at the exit end; and
    (g) detecting the presence of the target species.

12. The method of claim 11 further comprising forming an aerosol from the eluent exiting the capillary tube prior to detecting the presence of the target species.

13. The method of claim 12 wherein nitrogen gas injection is used to form the aerosol.

14. The method of claim 12 where the aerosol is an electrospray.

15. The method of claim 11 wherein the exit end of the capillary tube is interfaced with a mass spectrometer.

16. The method of claim 11 further comprising using alpha particles to ionize an inert gas to produce the electrically conducting gas.

17. The method of claim 16 wherein the alpha particles used to ionize the inert gas are emitted from thorium.

18. The method of claim 11 wherein the first electrical conducting terminal is maintained at a stable electrical potential of between about −30 kV and 30 kV.

19. The method of claim 11 wherein the second electrical conducting terminal is maintained at about ground potential.

20. A device for providing equal electrical potential between two loci unconnected by solid or liquid electrical conductors comprising:
    (a) a capillary tube having an exit end and a lumen;
    (b) a first electrical conducting terminal comprising a coating of silver paint on the exit end of the capillary tube extending into the lumen of the capillary tube;
    (c) a glass tube surrounding the exit end of the capillary tube having a shoulder distal to the exit end, which shoulder is sealed around the capillary tube;
    (d) a gas inlet fitting attached to the shoulder of the glass tube; and
    (e) a second electrical terminal comprising a metal tip attached to the glass tube so as to provide electrical continuity between the first terminal and the second terminal in an electroosmotic circuit when an electrically conductive gas is present in the glass tube.

* * * * *